United States Patent
Lecomte et al.

(10) Patent No.: US 11,285,238 B2
(45) Date of Patent: Mar. 29, 2022

(54) ADHESIVE INTERFACE BANDAGE

(71) Applicants: LABORATOIRES URGO, Chenove (FR); SOCIETE DE DEVELOPPEMENT ET DE RECHERCHE INDUSTRIELLE, Chenove (FR)

(72) Inventors: Serge Lecomte, Dijon (FR); Jean-Marc Pernot, Dijon (FR)

(73) Assignees: LABORATOIRES URGO, Chenove (FR); SOCIETE DE DEVELOPPEMENT ET DE RECHERCHE INDUSTRIELLE, Chenove (FR)

( * ) Notice: Subject to any disclaimer, the term of this patent is extended or adjusted under 35 U.S.C. 154(b) by 1055 days.

(21) Appl. No.: 14/366,190

(22) PCT Filed: Dec. 12, 2012

(86) PCT No.: PCT/FR2012/052897
§ 371 (c)(1),
(2) Date: Jun. 17, 2014

(87) PCT Pub. No.: WO2013/093298
PCT Pub. Date: Jun. 27, 2013

(65) Prior Publication Data
US 2014/0364788 A1    Dec. 11, 2014

(30) Foreign Application Priority Data

Dec. 19, 2011  (WO) ................ PCT/FR2011/053043

(51) Int. Cl.
*A61L 15/22*    (2006.01)
*A61F 13/00*    (2006.01)
(Continued)

(52) U.S. Cl.
CPC ............ *A61L 15/225* (2013.01); *A61F 13/00* (2013.01); *A61F 13/00017* (2013.01);
(Continued)

(58) Field of Classification Search
CPC .......... A61F 13/00004; A61F 13/00008; A61F 13/00017; A61F 13/00025;
(Continued)

(56) References Cited

U.S. PATENT DOCUMENTS 5,512,354 A * 4/1996 Scholz ................... D04B 21/12
442/306
6,270,792 B1 * 8/2001 Guillemet ......... A61F 13/00038
424/443
(Continued)

FOREIGN PATENT DOCUMENTS

EP    2168607    3/2010
FR    2936159    3/2010
(Continued)

OTHER PUBLICATIONS

WO 00/16725, translation.*

*Primary Examiner* — Camtu T Nguyen
(74) *Attorney, Agent, or Firm* — Hamre, Schumann, Mueller & Larson, P.C.

(57) ABSTRACT

The present invention relates to an adherent interface dressing intended for application directly to a wound. Said adherent interface dressing includes a non-adherent cohesive gel formed from a hydrophobic elastomeric matrix consisting of a styrene-(ethylene/butylene)-styrene or styrene-(ethylene/propylene)-styrene triblock elastomer optionally associated with a styrene-(ethylene/butylene) or styrene-(ethylene/propylene) diblock copolymer; said elastomer plasticized by means of a mineral oil, and containing dispersed therein a small quantity of hydrophilic particles of
(Continued)

a hydrocolloid; and a flexible open-mesh fabric, said fabric including threads coated with the non-adherent cohesive gel such as to leave the meshes substantially unsealed, The fabric is a heat-set knit with weft yarns, said yarns being continuous multifilament yarns with non-elastic filaments, whereof the extensibility in the transverse direction measured in accordance with standard EN 13726-4 is between 0.01 and 0.5 N/cm.

16 Claims, 1 Drawing Sheet

(51) Int. Cl.
*A61F 13/02* (2006.01)
*A61L 15/60* (2006.01)
*A61L 15/34* (2006.01)
*A61L 15/42* (2006.01)
*A61L 15/46* (2006.01)
*D04B 21/10* (2006.01)
*A61L 15/44* (2006.01)

(52) U.S. Cl.
CPC .. *A61F 13/00025* (2013.01); *A61F 13/00063* (2013.01); *A61F 13/02* (2013.01); *A61L 15/34* (2013.01); *A61L 15/42* (2013.01); *A61L 15/44* (2013.01); *A61L 15/46* (2013.01); *A61L 15/60* (2013.01); *D04B 21/10* (2013.01); *A61L 2300/404* (2013.01); *A61L 2300/406* (2013.01); *A61L 2300/606* (2013.01); *D10B 2509/022* (2013.01)

(58) Field of Classification Search
CPC ............... A61F 13/00063; A61F 13/02; A61F 13/0203; A61F 13/0213; A61F 13/0216; A61F 13/0223; A61F 13/0226; A61L 15/34; A61L 15/42; A61L 15/44; A61L 15/60; A61L 2300/404; A61L 2300/406; A61L 2300/606; D04B 21/10
USPC ...................................................... 602/44, 48
See application file for complete search history.

(56) References Cited

U.S. PATENT DOCUMENTS

| | | | | |
|---|---|---|---|---|
| 2004/0237599 | A1* | 12/2004 | Kondou | ............. D04B 1/18 66/202 |
| 2005/0228115 | A1* | 10/2005 | Auguste | ............. C08L 2666/24 524/505 |
| 2009/0192430 | A1* | 7/2009 | Evans | ............. A61F 13/04 602/44 |
| 2010/0076363 | A1 | 3/2010 | Staeger Williams et al. | |
| 2015/0174285 | A1* | 6/2015 | Auguste | ............. A61L 15/46 424/445 |

FOREIGN PATENT DOCUMENTS

| | | | |
|---|---|---|---|
| WO | WO 00/16725 | * | 9/1999 |
| WO | WO 00/16725 | * | 3/2000 |
| WO | WO 2005/056069 | | 6/2005 |

* cited by examiner

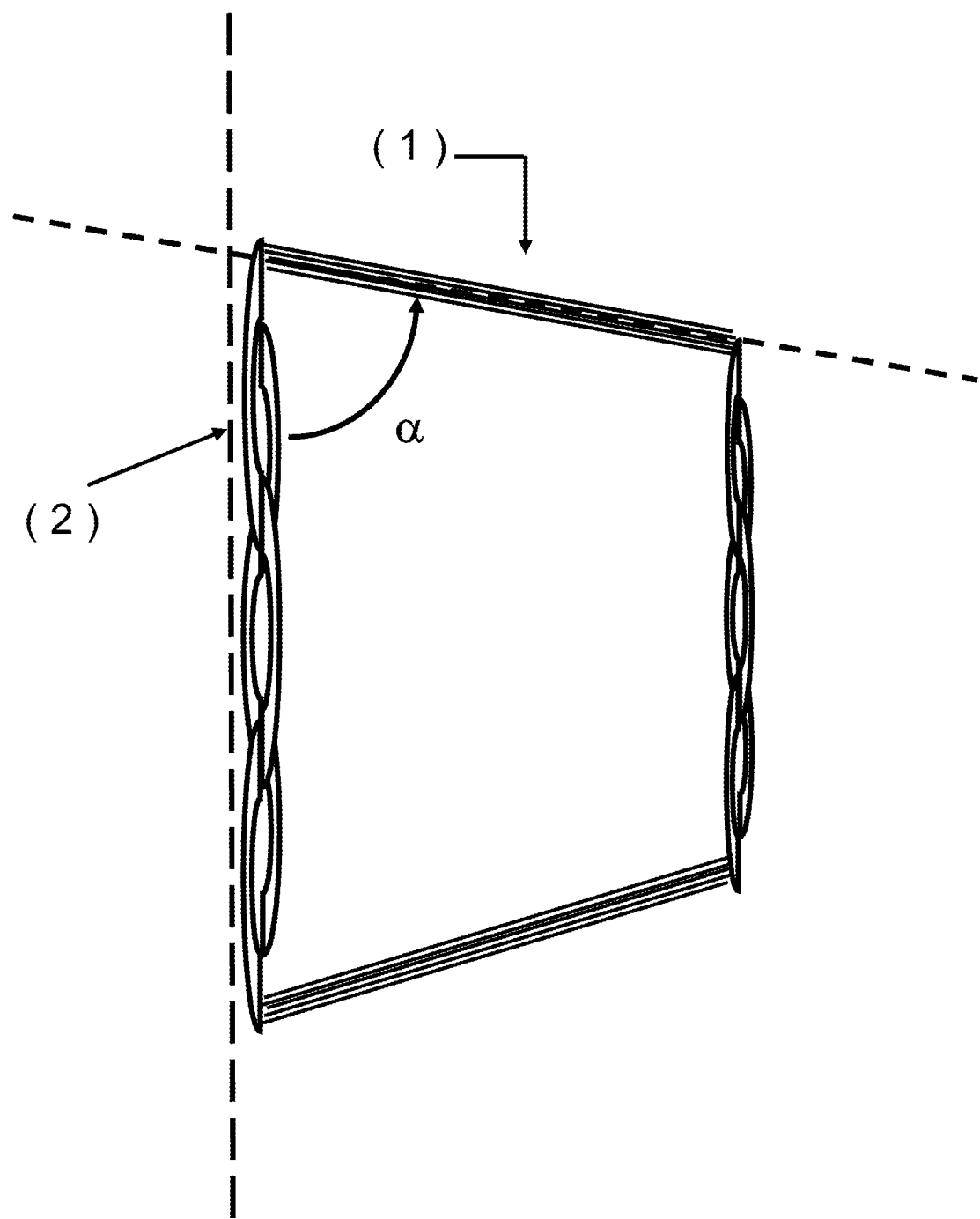

ADHESIVE INTERFACE BANDAGE

FIELD OF THE INVENTION

The present invention relates to an adherent interface dressing intended for application directly to a wound.

BACKGROUND

The treatment of wounds with dressings intended to be brought into contact with the wound while providing an interface between said wound and an absorbent compress, which is placed on the dressing in order to absorb the wound exudates, has been known for a long time. Such dressings are usually referred to as "interface dressings".

The interface dressing plus absorbent compress assembly is usually immobilized, either with a bandage that is wrapped around the part to be treated, for example around the arm or the leg, or with an adhesive tape.

Interface dressings are, for example, sold by the companies Laboratoires URGO or Molnlycke Health Care respectively under the names URGOTUL® and Mepitel®.

These products generally consist of a reinforcement made of an open-mesh fabric, the yarns of which are coated with a cohesive gel in such a way as to leave the meshes essentially unsealed.

Various studies have shown that the URGOTUL® interface dressing has notable properties with regard to the promotion of the healing process and in particular of fibroblast proliferation.

These advantageous properties do not appear to be the result of one particular component, but of the overall composition of the weakly absorbent, non-adherent, cohesive gel which coats the yarns of the flexible open-mesh fabric.

This gel is formed from a specific composition consisting of a highly plasticized, hydrophobic elastomeric matrix containing as a dispersion a small amount of hydrophilic particles of a hydrocolloid.

This dressing and this specific composition are described in patent application WO 00/16725.

The URGOTUL® product nevertheless has the drawback of not adhering to the skin.

Thus, according to the location of the wound on the body and in particular when the area of the wound is not flat, this dressing, once applied, rapidly falls off before the care staff have been able to apply the compress or definitively attach the interface plus compress assembly using a bandage.

It would therefore be desirable to have an interface dressing which has the advantageous properties of the URGOTUL® product but which has greater adherence to the skin in order to avoid this drawback.

Various solutions have been proposed for improving the properties of the product described in patent application WO 00/16725.

Thus, document WO 2005/056069 proposes preparing an interface dressing which comprises an absorbent matrix. However, the product described in said document remains non-adherent to the skin, and therefore suffers from the same drawbacks as the URGOTUL® product.

In order to increase the adherence of an absorbent or non-absorbent matrix, it can be envisioned to incorporate, into this matrix, an adherence-promoting additive such as a tackifying product.

The incorporation of a tackifying product in order to increase the adherence of the cohesive gel described in document WO 00/16725 nevertheless raises several difficulties.

The incorporation of tackifying compounds in fact modifies the rheological properties of the gel, which leads to very significant, or even insurmountable, technical difficulties for obtaining a correct coating of the threads of the fabric under economically acceptable industrial production conditions.

In order to solve these manufacturing problems, it has in particular been proposed, in document EP 2 168 607, to manufacture a self-supported product, thus avoiding a coating step. Such a product is capable of exhibiting better adherence through the obtaining of a "tacky" capacity.

However, all the solutions envisioned to date lead to the composition of the cohesive gel being reformulated and, consequently, require the use of new compounds.

It would be desirable, in order not to impair the efficiency of the process for manufacturing the product, nor to modify the latter, thus being sure to retain the notable healing properties of the formulations of the non-adherent and non-absorbent cohesive gel described in document WO 00/16725, to produce an adherent product without modifying the nature of the compounds used for producing this cohesive gel.

SUMMARY

Thus, the purpose of the present invention is to provide an interface dressing which is more adherent than the dressing described in document WO 00/16725, without modifying the nature of the compounds used, nor incorporating new compounds, in the formulation of the cohesive gel that it incorporates.

BRIEF DESCRIPTION OF THE DRAWINGS

FIG. 1 shows a mesh of a fabric of a dressing according to an embodiment.

DETAILED DESCRIPTION

Surprisingly, it has been found that the use of a particular fabric, namely a specific knit, makes it possible to produce an interface dressing which exhibits an adherence greater than that of the product described in document WO 00/16725, this being without adding or using new compounds in the formulation of the cohesive gel that it contains.

The present invention therefore relates to an adherent interface dressing comprising:
  a non-adherent cohesive gel formed from a hydrophobic elastomeric matrix consisting of a styrene-(ethylene/butylene)-styrene or styrene-(ethylene/propylene)-styrene triblock elastomer optionally combined with a styrene-(ethylene/butylene) or styrene-(ethylene/propylene) diblock copolymer, said elastomer being highly plasticized by means of a mineral oil, and containing as a dispersion a small amount of hydrophilic particles of a hydrocolloid; and
  a flexible open-mesh fabric, said fabric comprising yarns which are coated with the non-adherent cohesive gel in such a way as to leave the meshes essentially unsealed, characterized in that the fabric is a heat-set knit with weft yarns, said yarns being continuous multifilament yarns with non-elastic filaments, which exhibits an extensibility in the transverse direction, measured according to standard EN 13726-4, of between 0.01 and 0.5 N/cm.

In the context of the present invention, the hydrophobic elastomeric matrix comprises an elastomer chosen from triblock block polymers of the ABA type comprising two styrene end blocks A and one central block B which is a saturated olefin, for instance ethylene/butylene or ethylene/propylene.

These triblock copolymers can be optionally combined with diblock copolymers of the AB type comprising a styrene block A and an ethylene/propylene or ethylene/butylene block B.

In the case of a blend of triblock copolymers ABA and of diblock copolymers AB, it will be possible to use commercial blends of triblock copolymers ABA and of diblock copolymers AB which are already available, or to produce blends in any preselected proportion from two independently available products.

Such triblock copolymers comprising a saturated central block are well known to those skilled in the art and are, for example, sold:

by the company KRATON POLYMERS under the name KRATON G®, and in particular under the name KRATON G1651®, KRATON G1654® or KRATON G1652® for the poly(styrene-(-ethylene/butylene-)-styrene) (abbreviated to SEBS) block copolymers;

by the company KURARAY under the name SEPTON® for the poly(styrene-(-ethylene/propylene-)-styrene) (abbreviated to SEPS) block copolymers.

As an example of commercial blends of triblock and diblock copolymers, mention may be made of the product sold by the company KRATON POLYMERS under the name KRATON G1657®, the olefin block of which is ethylene/butylene.

As an example of a particular blend of triblock and diblock copolymers which can be produced in the context of the present invention, mention may be made of the blend:

of a triblock SEBS, such as in particular the product sold by the company KRATON POLYMERS under the name KRATON G1651®; and of a poly(styrene-olefin) diblock copolymer, such as in particular the poly(styrene-ethylene-propylene) sold by the company KRATON POLYMERS under the name KRATON G1702®.

In the context of the present invention, preference will be given to SEBS or SEPS triblock copolymers having a styrene content of between 25% and 45% by weight relative to the weight of said SEBS or SEPS and having a medium or high molecular weight and a Brookfield viscosity at least equal to 300 cp (measurement carried out at 25° C. for a solution at 10% in toluene).

Even more preferably, use will be made of triblock block copolymers alone, preferably SEBS triblock copolymers and in particular the products sold by the company KRATON POLYMERS under the names KRATON G1651® or KRATON G1654®.

The hydrophobic elastomer is plasticized by the addition of an oily element which makes it possible to obtain an elastic, highly cohesive gel with a fatty appearance.

In the context of the present invention, a mineral oil which has both good compatibility with the elastomers previously described and an acknowledged tolerance with respect to skin tissues will preferably be chosen as oily element. Liquid paraffins preferably of low viscosities or mixtures of liquid paraffin and of medicinal petroleum jelly will preferentially be used.

According to one variant of the present invention, a mineral oil combined with a small amount of vegetable oil may also be used.

Among the plasticizing oils which are particularly suitable, mention may be made of the products sold by the company SHELL under the names ONDINA® and RISELLA® which consist of a mixture based on naphthenic and paraffinic compounds.

Preferably, use will be made of a plasticizing oil chosen from the products sold under the names ONDINA 963®, ONDINA 15® and ONDINA 919® and in particular an oil sold under the name ONDINA 15® or ONDINA 919® in combination with a petroleum jelly in accordance with the French pharmacopeia.

Generally, the hydrophobic matrix comprises 1000 to 2000 parts by weight of liquid paraffin, preferably of low viscosity, and 0 to 400 parts by weight of petroleum jelly, per 100 parts by weight of elastomer.

According to one preferred embodiment of the invention, this matrix will comprise 100 parts by weight of high-molecular-weight SEBS elastomer, for instance KRATON G 1651®, and 1600 parts by weight of an oily plasticizer composed of 95% by weight of low-viscosity liquid paraffin and 5% by weight of petroleum jelly.

As previously indicated, the hydrophobic matrix also contains, as a dispersion, a small amount of hydrophilic particles of a hydrocolloid.

The term "hydrocolloid" or "hydrocolloid particles" is intended to denote here any compound normally used by those skilled in the art for its ability to absorb aqueous liquids such as water, physiological saline or the exudates from a wound.

As suitable hydrocolloids, mention may be made, for example, of pectin, alginates and carboxymethylcellulose and its salts of an alkali metal such as sodium and calcium.

The hydrocolloids which are preferred in the context of the present invention are the alkali metal salts of carboxymethylcellulose, in particular sodium carboxymethylcellulose (CMC).

The size of the hydrocolloid particles is advantageously between 50 and 100 microns, in particular about 80 microns.

The amount of hydrocolloids incorporated into the elastomer composition will advantageously be about from 2% to 20% by weight, preferably from 5% to 18% by weight and more preferably from 12% to 16% by weight, relative to the total weight of the elastomeric matrix.

The elastomeric matrix may also comprise one or more antioxidants.

As examples of suitable antioxidants, mention may be made of:

phenolic antioxidants, such as in particular the products sold by the company CIBA SPECIALTY CHEMICALS under the names IRGANOX 1010®, IRGANOX 565® and IRGANOX 1076®.

These antioxidants may be used in an amount of about from 0.05% to 1% by weight, preferably from 0.1% to 0.5% by weight, relative to the total weight of the elastomeric matrix.

In the context of the present invention, the use of the product IRGANOX 1010® will be preferred.

The elastomeric matrix can also contain active ingredients which have a favorable role in the treatment of the wound. These active ingredients may in particular induce or accelerate healing.

These active agents may be used in an amount of about from 0.01% to 20% by weight, preferably from 1% to 15% by weight and in particular from 2% to 10% by weight relative to the total weight of the elastomeric matrix.

Among the active substances which can be used in the context of the invention, mention may be made, by way of examples, of antiseptics, antibiotics, bactericidal agents or bacteriostatic agents, agents which promote healing, painkillers or anti-inflammatories.

In the context of the present invention, the reinforcement of the dressing is an open-mesh fabric made up of a specific knit.

When studying the removal of an interface dressing from the wound, the inventor has noted that the adherence to the skin depends not only on the nature of the gel, but also on the nature of the fabric onto which the gel is coated.

It has thus been determined, entirely unexpectedly, that a heat-set knit with weft yarns which has a particular level of extensibility in the transverse direction, when it is subjected to weak strains, makes it possible to obtain an adherent product without modifying the nature of the constituents of the cohesive gel.

The essential characteristic of such a knit is to exhibit, in the transverse direction, an extensibility, measured according to standard NF EN 13726-4, of between 0.01 and 0.5 N/cm.

Preferably, this extensibility will be between 0.05 and 0.3 N/cm and more preferably between 0.08 and 0.15 N/cm.

According to a preferred version of the present invention, this knit will exhibit, in the longitudinal direction, an extensibility, measured according to the same standard, of between 15 and 30 N/cm and preferably between 20 and 25 N/cm. Such an extensibility in the longitudinal direction in fact enables coating of the knit with the cohesive gel which is easier and more even from an industrial point of view.

Generally, this knit is made with weft yarns, and will in particular be manufactured according to the "warp knitting" technology.

Furthermore, this knit is heat-set.

This heat-setting makes it possible to dimensionally stabilize the structure of the knit after knitting via a thermal effect. This heat-setting operation is commonly used by those skilled in the art in the manufacture of a knit of which it is desired to fix the three-dimensional structure. It can be carried out using various technologies, either by passing the knit through a series of thermoregulated ovens, or by passing the knit through an autoclave, or else by passing the knit between one or more heated rolls. In the context of the present invention, it will be preferred to carry out this heat-setting operation by passing the knit between two heated rolls.

According to the invention, this knit is produced using continuous multifilament yarns with non-elastic filaments. The term "filament yarn" is intended to mean a yarn formed from one or more long twisted filaments.

This yarn will preferably be chosen from yarns of 33 to 115 dtex comprising 12 to 36 filaments.

The constituent material of the yarns is preferably synthetic and hydrophobic in nature. This material is advantageously chosen from polyesters and polyamides.

According to the preferred version of the invention, a heat-set knit with weft yarns based on 50-dtex polyester continuous multifilament yarns comprising 24 filaments will be used.

This knit may have a grammage of between 20 and 40 g/m$^2$ and preferably between 24 and 32 g/m$^2$.

This knit may have rectangular, square or polygonal meshes.

These meshes will advantageously have openings, the unit area of which before coating is about from 0.5 to 3 mm$^2$ and preferably between 0.85 and 1.25 mm$^2$.

According to a preferred version of the present invention, a knit which has trapezoidal meshes will be used. A knit with such a mesh is illustrated diagrammatically in FIG. 1. The angle $\alpha$ is defined as the average join angle of the rows (1) and the columns (2) of the knit.

According to the preferred version of the present invention, this knit has an average mesh surface area of about 0.95 mm$^2$ and an angle $\alpha$ as described in FIG. 1 of between 75 and 85 degrees.

The coating of the cohesive gel onto the knit is carried out so as to leave the meshes essentially unsealed, according to techniques known to those skilled in the art and so as to obtain a coating which ranges from 110 to 160 g/m$^2$ and preferably from 125 to 135 g/m$^2$.

In the context of the present invention, the process described in patent application WO 00/16725 will preferably be carried out in order to perform this coating.

The appended FIG. 1 represents, diagrammatically, a mesh of the fabric of a dressing according to one preferred embodiment of the invention.

The invention will be illustrated by the examples and the comparative test which follow.

Comparative Example

An URGOTUL® interface dressing was used as comparative example. The composition of the gel and the production of such a dressing is described in example 1 of patent application WO 00/16725.

In this comparative example, the fabric was a heat-set marquisette made of polyester yarns, manufactured by the company MDB TEXINOV under the reference 555. The grammage thereof is 45 g/m$^2$.

This marquisette exhibited an extensibility, measured according to standard EN 13726-4, of 2.7 N/cm in the transverse direction and of 24 N/cm in the longitudinal direction.

Example According to the Invention

A dressing according to the invention was produced according to the same manufacturing process and with the same gel composition as in example 1 of patent application WO 00/16275, but replacing the marquisette with a heat-set knit with weft yarns, made of polyester yarns, manufactured by the company MDB TEXINOV under the reference 601. The grammage thereof was 28 g/m$^2$.

This knit exhibited an extensibility, measured according to standard EN 13726-4, of 0.09 N/cm in the transverse direction and of 24 N/cm in the longitudinal direction.

Demonstration of the Adherence of the Dressing According to the Invention on the Skin:

In order to illustrate the greater adherence of the product according to the invention compared with the URGOTUL® product, a comparative in vivo test was carried out.

The protocol of this test was the following:
cut 4 samples of 5×5 cm format from a dressing 10×10 cm in size without removing the two protective films,
take a sample and remove one of the two protective films,
bend the forearm toward the arm (elbow forwards),
with the other hand, apply to the elbow the face of the sample devoid of protective film while pressing lightly,
remove the second protective film,
wait 10 seconds and note whether the sample falls off or remains in place.

The elbow was cleaned with soapy water, and dried with a paper tissue and the operation was recommenced with another sample.

In order to obtain significant and reproducible results, 2 samples of the same dressing were tested on the left elbow and 2 other samples were tested on the right elbow.

This protocol was reproduced 10 times while cutting out the samples once in the longitudinal direction and once in the transverse direction, i.e. a total of 40 samples tested.

A second series of tests was carried out with a second tester, i.e. again 40 samples tested.

This test is particularly discriminating since the bend of the elbow is an area to which it is always difficult to get a product to adhere. It also illustrates the steps carried out by the care staff who apply the interface dressing.

The results that were obtained are collated in table 1 hereinafter.

TABLE 1

| Product | Cut | according to the invention | URGOTUL ® |
|---|---|---|---|
|  |  | Left elbow | Right elbow |
| Tester 1 | transverse | 9/10 | 2/10 |
|  | longitudinal | 8/10 | 1/10 |
|  |  | Right elbow | Left elbow |
| Tester 2 | transverse | 9/10 | 1/10 |
|  | longitudinal | 10/10 | 2/10 |

The results of table 1 illustrate the advantages of the product according to the invention compared with the URGOTUL® product.

The product according to the invention virtually never falls off regardless of the tester, the elbow tested and the direction in which the sample was cut from the dressing and this result is reproducible with several dressings. It fell off only 4 times out of 40 tests.

Conversely, the URGOTUL® product fell off virtually systematically. It stayed in place only 5 times out of 40 tests.

Except for 10% of the tests carried out, which represents the uncertainties of measurement associated with the nature of the skin of the elbow and of the tester and the variabilities regarding the manufacturing of the dressing, a very significant difference in behavior in terms of adherence was thus observed between the dressing according to the invention and the URGOTUL® product.

The invention claimed is:

1. An adherent interface dressing comprising:
   a non-adherent cohesive gel formed from a hydrophobic elastomeric matrix comprising: an elastomer, wherein the elastomer is a styrene-(ethylene/butylene)-styrene triblock elastomer or a styrene-(ethylene/propylene)-styrene triblock elastomer, and a plasticizer comprising a mineral oil, and a dispersed small amount of hydrophilic particles of a hydrocolloid; and
   a flexible open-mesh fabric, said flexible open-mesh fabric comprising yarns which are coated with the non-adherent cohesive gel in such a way as to leave openings of the open-mesh essentially unsealed,
   wherein the flexible open-mesh fabric is a heat-set knit with weft yarns, said weft yarns being continuous multifilament yarns with non-elastic filaments, said heat-set knit exhibiting an extensibility in the transverse direction, measured according to standard EN 13726-4, of between 0.01 and 0.5 N/cm, wherein the heat-set knit has a grammage of between 24 g/cm$^2$ and 40 g/cm$^2$, and wherein the heat-set knit includes a trapezoidal knit and an average join angle of rows and columns of said trapezoidal knit is between 75 degrees and 85 degrees.

2. The dressing as claimed in claim 1, wherein the yarns constituting the knit are chosen from yarns of 33 to 115 dtex comprising 12 to 36 filaments.

3. The dressing as claimed in claim 1, wherein the yarns constituting the heat-set knit are made of polyamide or of polyester.

4. The dressing as claimed in claim 1, wherein the hydrophobic elastomeric matrix further comprises a styrene-(ethylene/butylene) diblock copolymer or a styrene-(ethylene/propylene) diblock copolymer.

5. The dressing as claimed in claim 1, wherein the heat-set knit exhibits an extensibility in the longitudinal direction, measured according to standard EN 13726-4, of between 15 and 30 N/cm.

6. The dressing as claimed in claim 1, wherein the mineral oil is a liquid paraffin or a mixture of liquid paraffin and of petroleum jelly.

7. The dressing as claimed in claim 1, wherein the elastomer is the styrene-(ethylene/butylene)-styrene triblock elastomer, and the plasticizer comprises 1000 to 2000 parts by weight of liquid paraffin and 0 to 400 parts by weight of medicinal petroleum jelly per 100 parts by weight of the elastomer.

8. The dressing as claimed in claim 1, wherein the hydrocolloid is sodium carboxymethylcellulose.

9. The dressing as claimed in claim 1, wherein the hydrocolloid is present in an amount of from 2% to 20% of the weight relative to the total weight of the hydrophobic elastomeric matrix.

10. The dressing as claimed in claim 1, wherein the hydrophobic elastomeric matrix further comprises an active agent.

11. The dressing as claimed in claim 10, wherein the active agent is selected from the group consisting of an antiseptic, an antibiotic and a compound which promotes wound healing.

12. The dressing as claimed in claim 1, wherein the heat-set knit exhibits an extensibility in the longitudinal direction, measured according to standard EN 13726-4, of between 15 and 30 N/cm.

13. The dressing as claimed in claim 1, wherein the elastomer is the styrene-(ethylene/butylene)-styrene triblock elastomer, the plasticizer comprises 1000 to 2000 parts by weight of liquid paraffin and 0 to 400 parts by weight of medicinal petroleum jelly per 100 parts by weight the elastomer, and the hydrocolloid is sodium carboxymethylcellulose.

14. The dressing as claimed in claim 13, wherein the hydrocolloid is present in an amount of from 2% to 20% of the weight relative to the total weight of the hydrophobic elastomeric matrix.

15. The dressing as claimed in claim 13, wherein the hydrophobic elastomeric matrix further comprises an active agent.

16. The dressing as claimed in claim 15, wherein the active agent is selected from the group consisting of an antiseptic, an antibiotic and a compound which promotes wound healing.

* * * * *